United States Patent
Wu et al.

(10) Patent No.: US 6,685,720 B1
(45) Date of Patent: Feb. 3, 2004

(54) CATHETER HAVING IMPROVED SHAPED RETENTION

(75) Inventors: Show-Mean Wu, San Diego, CA (US); Ricardo Roman, San Diego, CA (US)

(73) Assignee: Interventional Technologies, San Diego, CA (US)

( * ) Notice: Subject to any disclaimer, the term of this patent is extended or adjusted under 35 U.S.C. 154(b) by 427 days.

(21) Appl. No.: 09/690,187

(22) Filed: Oct. 16, 2000

(51) Int. Cl.[7] ............................................. A61M 29/00
(52) U.S. Cl. .................. 606/192; 604/103.09
(58) Field of Search ................. 606/192–194, 606/108, 200; 623/1.11, 1.23; 604/96.01, 103, 103.04, 103.09, 915, 919, 921; 600/435, 466, 467

(56) References Cited

U.S. PATENT DOCUMENTS

| | | |
|---|---|---|
| 4,608,984 A | 9/1986 | Fogarty |
| 4,627,436 A | 12/1986 | Leckrone |
| 4,685,458 A | 8/1987 | Leckrone |
| 5,042,985 A | 8/1991 | Elliott |
| 5,050,606 A * | 9/1991 | Tremulis ..................... 600/486 |
| 5,156,594 A | 10/1992 | Keith |
| 5,295,962 A | 3/1994 | Crocker |
| 5,300,025 A * | 4/1994 | Wantink ................. 604/103.09 |
| 5,322,508 A | 6/1994 | Viera |
| 5,346,464 A | 9/1994 | Camras |
| 5,354,279 A | 10/1994 | Hofling |
| 5,549,552 A | 8/1996 | Peters |
| 5,823,995 A * | 10/1998 | Fitzmaurice et al. ... 604/103.09 |
| 6,068,623 A | 5/2000 | Azdno-Azizi |
| 6,171,279 B1 * | 1/2001 | Hilaire et al. ............ 604/96.01 |

FOREIGN PATENT DOCUMENTS

| | | |
|---|---|---|
| CN | 1061704 A | 6/1992 |
| WO | WO 93/17750 | 10/1993 |
| WO | WO 99/44667 | 10/1999 |

* cited by examiner

*Primary Examiner*—Michael J. Milano
*Assistant Examiner*—(Jackie) Tan-Uyen T. Ho
(74) *Attorney, Agent, or Firm*—Nydegger & Associates

(57) ABSTRACT

A catheter for use in a body vessel includes a relatively stiff proximal shaft that is shaped as a tube formed with a lumen and having a proximal end and a distal end. Further, the catheter includes a relatively flexible distal tube formed with a lumen and having a proximal end and a distal end. An inflatable balloon may be attached to the outer wall of the distal tube near the distal end. The proximal end of the distal tube is attached to the distal end of the proximal shaft at a transitional joint. The transitional joint provides a gradual transition in flexibility over the length of the joint between the stiff proximal shaft and the flexible distal tube. Importantly, the transitional joint includes an extension made of a material having superelastic properties when positioned inside the body vessel. One end of the extension is attached to the distal end of the proximal shaft. The other end of the extension projects into the lumen of the distal tube. The extension may be formed as a ribbon, core wire or may constitute a tapered section of the proximal shaft.

18 Claims, 2 Drawing Sheets

CATHETER HAVING IMPROVED SHAPED RETENTION

FIELD OF THE INVENTION

The present invention pertains generally to medical catheters and methods for manufacturing medical catheters. More particularly, the present invention pertains to medical catheters having improved shape retention. The present invention is particularly, but not exclusively, useful as an angioplasty catheter for movement through vessels wherein turns of up to 120 degrees are required.

BACKGROUND OF THE INVENTION

Intravascular procedures are commonly utilized to treat a stenosis within a vessel or artery of a human. One procedure used to treat a stenosis is commonly referred to as angioplasty. During an angioplasty procedure, a guidewire is first positioned in the vessel to establish a mechanical pathway to the stenosis. Next, a balloon catheter is placed over the guidewire and pushed through the vasculature until the balloon is adjacent the stenosis. Finally, the balloon is inflated to compress the stenosis and thereby dilate the lumen of the vessel.

The human vasculature is curved, branched and contains vessels having relatively small inner diameters. As a result thereof, the doctor or physician often needs to maneuver and twist the catheter to move the catheter through the body vessel. In some circumstances, for example near the aorta, the catheter must be capable of bending over 120 degrees as it is advanced through the curved vessel. To do this, the shaft of the catheter must have good strength and stiffness to withstand the axial and torsional forces which occur as the catheter is pushed and steered through the vasculature. Additionally, however, the catheter shaft must be sufficiently flexible to allow the catheter to track the guidewire.

The tradeoff between stiffness and flexibility may be partially overcome by using a two-part catheter shaft. Specifically, the distal portion of the shaft, where flexibility is required for adequate tracking, can be made of a flexible material such as plastic. On the other hand, in the proximal portion of the shaft, where more strength and stiffness are required for adequate pushability, the shaft can be made from a metallic material such as stainless steel. Unfortunately, for such a two-part construction, the area of the catheter shaft near the joint between the flexible portion and the stiff portion is generally subject to kinking. In particular, when the catheter shaft is made to bend through angles of up to 120 degrees, the area near the joint absorbs nearly all the stress of the bend. The result can be a sharp bend in which permanent deformation occurs. This permanent deformation or kink does not recover as the joint area subsequently passes into straighter vessel paths. Rather, the kink interferes with and limits the subsequent movement of the catheter throughout the vasculature.

Certain alloys, called shape-memory alloys, are known for their ability to recover large strains (up to approximately 8 percent). As is well known, the crystal structure of alloys can be manipulated by thermal treatments and other processes to alter the microstructure of the alloy from one crystal structure to another. Each crystal structure is known as a phase, such as an austenite phase or a martensite phase, and the change from one phase to another is termed a phase transformation. To use a traditional shape-memory alloy, a part is initially shaped from the alloy at a first temperature, above the phase transformation temperature. Next, the shaped part can be cooled to a second temperature, below the phase transformation temperature, thus inducing a phase transformation such as an austenite to martensite phase transformation. At the lower temperature, while the alloy is in the martensite phase, a stress can be applied to deform the part to strains of up to approximately 8 percent. Upon release of the applied stress, the 8 percent strain will remain. Next, the deformed part can be heated back above the phase transformation temperature, thereby transforming the alloy back to the austenite phase. During this last phase transformation, the strain will be recovered, and the original (unstrained) shape of the part will return.

Some shape memory alloys will isothermally transform from the austenite phase to the martensite phase in response to an applied stress. These alloys are called stress-induced martensite (SIM) alloys. For example, at a temperature slightly above the austenite to martensite phase transformation temperature, the SIM alloy can be isothermally deformed (up to 8 percent) causing the alloy to transform from the austenite to the martensite phase. In the absence of the phase transformation, a strain of 8 percent could not be recovered. In the SIM alloy, when the stress is removed, the alloy will return to the austenite phase and strain will be recovered. Importantly, the strain and recovery process in SIM alloys can occur isothermally. The ability of SIM alloys to recover large strains isothermally through the phase transformation process is termed superelasticity.

Importantly for the present invention, some SIM alloys are known in the art, such as some nickel-titanium alloys, that have an austenite to martensite phase transformation temperature slightly below the human body temperature. Consequently, in light of the above discussion, these alloys are superelastic when positioned inside a body vessel. When a part made from these alloys is inserted into the body and subsequently placed under stress creating deformations of up to 8 percent, these deformations or strains can be recovered when the stress is removed. For example, a catheter shaft made of a SIM alloy may bend while negotiating a 120 degree curve in a vessel. During the bend, strains of up to 8 percent may occur near the outer radius of the shaft. As the deformed portion of the shaft is advanced from the curved portion of the vessel to a straighter vessel portion, the stress from the bend will recover, and the deformed portion of the shaft will return to its original shape.

In light of the above, it is an object of the present invention to provide a catheter and a method of manufacturing a catheter having good pushability and trackability in the body vessel. Another object of the present invention is to provide a catheter and a method of manufacturing a catheter that can traverse a path having a 120 degree bend within the vasculature of a patient without kinking. Still another object of the present invention is to provide a catheter and a method of manufacturing a catheter having good flexibility, durability, and torsional strength characteristics. Another object of the present invention is to provide a joint that creates a gradual transition between a stiff proximal shaft and a flexible distal tube. Yet another object of the present invention is to provide a catheter which is relatively simple to manufacture, is easy to use, and is comparatively cost effective.

SUMMARY OF THE PREFERRED EMBODIMENTS

The present invention is directed to a catheter and a method for manufacturing a catheter for use in a body vessel. For the present invention, the catheter includes a relatively stiff proximal shaft that is shaped as a tube formed with a lumen and having a proximal end and a distal end. Further, the catheter includes a relatively flexible distal tube formed with a lumen and having a proximal end and a distal end. Each tube has an inner wall and an outer wall. An inflatable balloon may be attached to the outer wall of the distal tube near the distal end. The proximal end of the distal tube is attached to the distal end of the proximal shaft at a transitional joint which provides a gradual transition in flexibility over the length of the joint between the stiff proximal shaft and the flexible distal tube.

Importantly, the transitional joint for the catheter of the present invention includes an extension made of a material having superelastic properties when positioned inside the body vessel. Functionally, the extension allows for the gradual transition in flexibility required in the joint section. One end of the extension is attached to the distal end of the proximal shaft. The other end of the extension projects into the lumen of the distal tube. The extension may be formed as a ribbon, core wire or may constitute a tapered section of the proximal shaft. Using these component elements, at least three embodiments for a transitional joint are contemplated for the present invention for interconnecting the distal tube, the extension, and the proximal shaft.

In a first embodiment, in addition to the distal tube, extension, and proximal shaft, the transitional joint includes an extension tube and an insert. Preferably, the extension tube and insert are made from a material having superelastic properties when positioned inside the body vessel. In this embodiment, one end of the insert is disposed within the lumen of the proximal shaft and is affixed to the inner wall of the proximal shaft. The second end of the insert is disposed within the lumen of the extension tube and is affixed to the inner wall of the extension tube. Further, the extension is affixed to the outer wall of the extension tube, thereby becoming attached to the proximal shaft. The extension then projects into the lumen of the distal tube. In this embodiment, the inner wall near the proximal end of the distal tube is affixed to the outer wall of the extension tube, thereby attaching the distal tube to the proximal shaft.

In another embodiment of the transitional joint for attaching both the distal tube and the extension to the proximal shaft, a tapered section formed integrally with the proximal shaft and extending from the distal end of the proximal shaft constitutes the extension. In this embodiment, the tapered section (extension) projects into the lumen of the distal tube. The inner wall near the proximal end of the distal tube is bonded to the outer wall of the proximal shaft near its distal end. Preferably, in this embodiment, both the proximal shaft and extension are made from a material having superelastic properties when positioned inside the body vessel.

In yet another embodiment of the transitional joint for attaching both the distal tube and the extension to the proximal shaft, the catheter includes a coil spring made from a material having superelastic properties when positioned inside the body vessel. The coil spring has an inner wall and an outer wall, and is formed with a lumen. Further, the coil spring has a proximal end and a distal end. In this embodiment, the distal end of the proximal shaft is deformed or collapsed. This deformation results in a portion of the outer wall of the proximal shaft at the distal end having a concave surface. The inner wall of the coil spring near the proximal end is affixed to the outer wall of the proximal shaft adjacent and proximal to the concave surface. The outer wall near the distal end of the coil spring is affixed to the inner wall of the distal tube thereby attaching the distal tube to the proximal shaft. In this embodiment, the extension is preferably a core wire. One end of the core wire is affixed to the concave surface of the proximal shaft and the other end of the core wire projects through the lumen of the coil spring and into the lumen of the distal tube.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
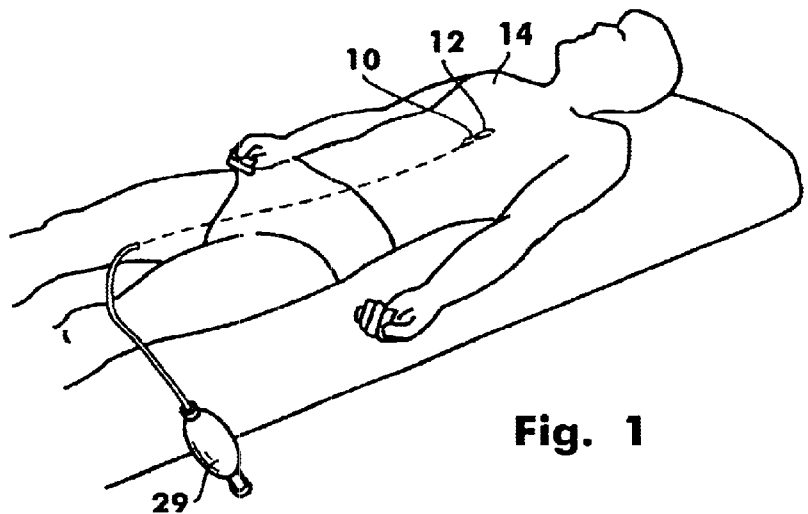
FIG. 1 is a perspective view of a portion of a catheter having features of the present invention operationally positioned in the vasculature of a patient.
Figure 2:
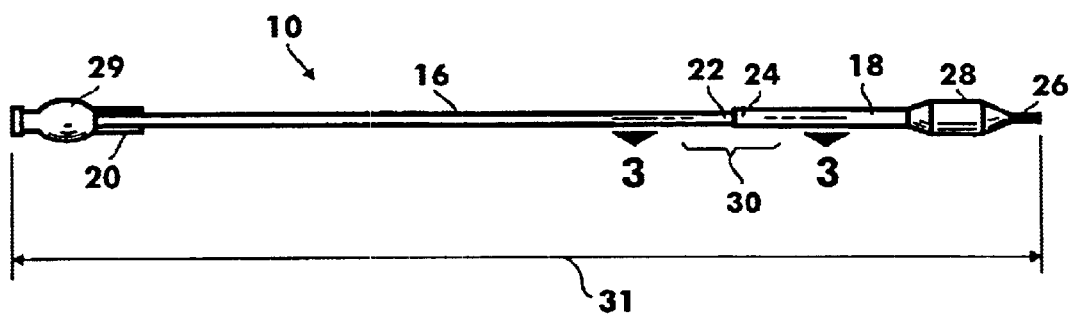
FIG. 2 is an elevational view of a catheter having features of the present invention.

Referring initially to FIG. 1, a catheter 10 in accordance with the present invention is shown inserted into the vessel 12 of a patient 14. For the present invention, the catheter 10 includes a proximal shaft 16 and a distal tube 18 as shown in FIG. 2. The proximal shaft 16 is preferably formed as a tube, but may be solid. The proximal shaft 16 has a proximal end 20 and a distal end 22. Similarly, the distal tube 18 has a proximal end 24 and a distal end 26. An inflatable balloon 28 may be attached to the distal tube 18 near the distal end 26. A manifold 29 is shown attached to the proximal end 20 of the proximal shaft 16. As further shown in FIG. 2, the proximal end 24 of the distal tube 18 is attached to the distal end 22 of the proximal shaft 16 at a transitional joint 30. The overall length 31 of the catheter 10 is preferably between approximately 130 centimeters and 150 centimeters.

Figure 3:
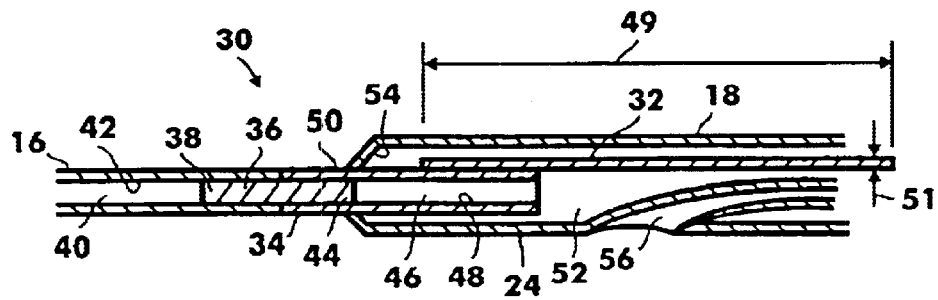
FIG. 3 is a cross sectional view of a portion of the catheter of the present invention as seen along line 3—3 in FIG. 2 showing a first embodiment of a transitional joint between a proximal shaft and a distal tube.

Importantly, the catheter 10 of the present invention includes an extension 32 as shown in FIG. 3, made of a material having superelastic properties when positioned inside the body vessel. For purposes of the present invention, the term "superelastic properties" means the material can experience an isothermal phase transformation with the ability to recover strains of up to 8 percent upon the removal of an applied stress. With this in mind, the extension 32 is made of a material having superelastic properties and it may be formed as a ribbon, or as a core wire, or it may constitute a tapered section of the proximal shaft 16. A suitable superelastic material for this purpose includes the Nitinol alloys which are alloys having approximately equal parts of nickel and titanium. TINEL™ sold by Raychem is one such alloy. As indicated above, for the material to be superelastic during use in the body vessel, the phase transformation temperature of the alloy must be slightly below the ambient temperature of the body vessel, allowing the alloy to undergo a stress-induced martensite transformation. Other suitable alloys include CuZnAl alloys and CuAlNi alloys. In accordance with the manufacturing method of the present invention, the structures herein disclosed that are preferably formed of a superelastic material should be shaped at a temperature sufficiently above the phase transformation temperature such that the material after shaping is entirely in the austenite phase. Next, the austenitized and shaped part is allowed to cool to room temperature for subsequent use within a body vessel.

Figure 4:
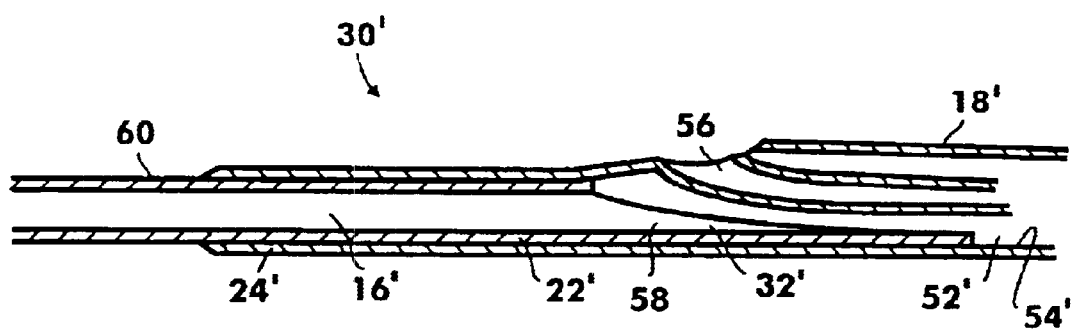
FIG. 4 is a cross sectional view of a portion of the catheter as in FIG. 3 showing an alternative embodiment of a transitional joint between a proximal shaft and a distal tube.
Figure 5:
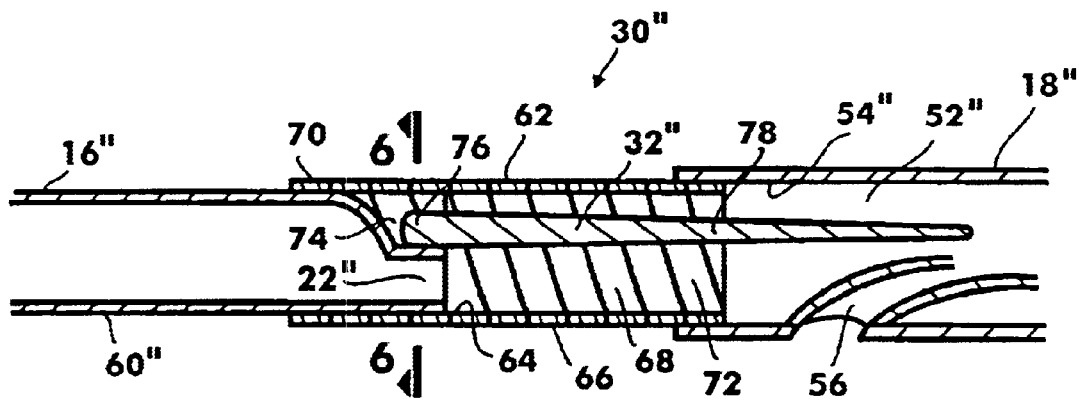
FIG. 5 is a cross sectional view of a portion of the catheter as in FIG. 3 showing yet another alternative embodiment of a transitional joint between a proximal shaft and a distal tube.

Three embodiments of a transitional joint 30 for attaching both the distal tube 18 and the extension 32 to the proximal shaft 16 are contemplated for the present invention and shown in FIGS. 3, 4 and 5. For the embodiment shown in FIG. 3, the transitional joint 30 includes an extension tube 34 and an insert 36. Preferably, the extension tube 34 and insert 36 are made from a material having superelastic properties when positioned inside the body vessel. In this embodiment, an end 38 of the insert 36 is disposed within the lumen 40 of the proximal shaft 16 and is affixed to the inner wall 42 of the proximal shaft 16. Preferably, in this embodiment, the proximal shaft 16 is made of either stainless steel or a superelastic material. The second end 44 of the insert 36 is disposed within the lumen 46 of the extension tube 34 and affixed to the inner wall 48 of the extension tube 34. Further, the extension 32 is affixed to the outer wall 50 of the extension tube 34, thereby becoming attached to the proximal shaft 16. In this embodiment, the extension 32 is preferably shaped as a ribbon having a length 49 of between approximately 15 centimeters and 30 centimeters and a width 51 of between approximately 0.003 inches and 0.010 inches. The extension 32 projects into the lumen 52 of the distal tube 18. In this embodiment, the inner wall 54 of the distal tube 18 near the proximal end 24 is affixed to the outer wall 50 of the extension tube 34, thereby attaching the distal tube 18 to the proximal shaft 16. In this embodiment, the distal tube 18 is preferably made of a polymer material such as PEBA, PET, Polyurethane, Polyethylene or nylon. Also shown in FIG. 3, a guidewire lumen 56 is provided near the transitional joint 30.

An alternative embodiment of a transitional joint (designated 30') for attaching both the distal tube 18' and the extension 32' to the proximal shaft 16' is shown in FIG. 4. As shown, the extension 32' is a tapered section 58 that is formed integrally with the proximal shaft 16' and extends from the distal end 22' of the proximal shaft 16'. In the embodiment shown in FIG. 4, the tapered section 58 projects into the lumen 52' of the distal tube 18'. The inner wall 54' of the distal tube 18' near the proximal end 24' is bonded to the outer wall 60 of the proximal shaft 16' near the distal end 22'. Preferably, in the embodiment shown in FIG. 4, both the proximal shaft 16' and extension 32' are made from a material having superelastic properties when positioned inside the body vessel.

Figure 6:
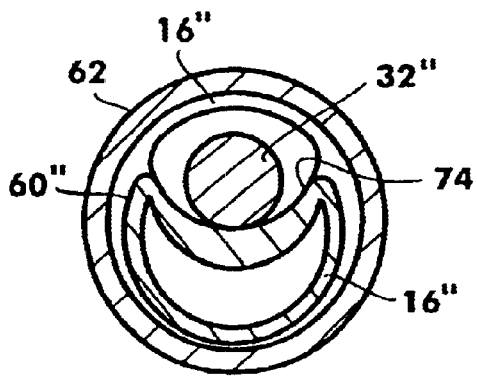
FIG. 6 is a cross sectional view of a catheter having features of the present invention as seen along line 6—6 in FIG. 5 showing the deformed end of the proximal shaft and the core wire.

FIG. 5 shows yet another alternative embodiment of the transitional joint 30" for attaching both the distal tube 18" and the extension 32" to the proximal shaft 16". As shown in FIG. 5, this embodiment of transitional joint 30" includes a coil spring 62 that is preferably made from a material having superelastic properties when positioned inside the body vessel. The coil spring 62 has an inner wall 64, and outer wall 66 and is formed with a lumen 68. Further, the coil spring 62 has a proximal end 70 and a distal end 72. By cross-referencing FIGS. 5 and 6, it can be seen that the distal end 22" of the proximal shaft 16" is deformed (i.e. collapsed). This deformation results in a portion of the outer wall 60" of the proximal shaft 16" at the distal end 22" having a concave surface 74. The inner wall 64 of the coil spring 62 near the proximal end 70 is affixed to the outer wall 60" of the proximal shaft 16" adjacent and proximal to the concave surface 74. The outer wall 66 of the coil spring 62 near the distal end 72 is affixed to the inner wall 54" of the distal tube 18", thereby attaching the distal tube 18" to the proximal shaft 16". In this embodiment, the extension 32" is preferably a core wire. One end 76 of the extension 32" is affixed to the concave surface 74 of the proximal shaft 16" and the other end 78 of the extension 32" projects through the lumen 68 of the coil spring 62 and into the lumen 52" of the distal tube 18". Any method known in the pertinent art for affixing the extension 32" to the proximal shaft 16", such as brazing or bonding, may be used.

While the particular catheter and method of manufacturing a catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A catheter for use within a body vessel having an ambient body vessel temperature, T, the catheter comprising:

a distal tube having a proximal end and a distal end and formed with a lumen; and a proximal shaft attached to said distal tube; and an extension attached to said proximal shaft and projecting therefrom into said lumen of said distal tube, said extension made from a superelastic material which undergoes an isothermal phase transformation at said ambient body vessel temperature, T when strained in response to an applied stress and recovers at least a part of said strain in an isothermal phase transformation when said applied stress is removed to provide shape retention to said catheter.

2. The catheter as recited in claim 1 wherein said proximal shaft is formed integrally with said extension.

3. The catheter as recited in claim 1 further comprising a coil spring surrounding said extension, wherein said distal tube is attached to said proximal shaft by said coil spring, said coil spring having a first end affixed to said distal tube and a second end affixed to said proximal shaft.

4. The catheter as recited in claim 3 wherein said coil spring is made from a superelastic material which undergoes an isothermal phase transformation at said ambient body vessel temperature, T when strained in response to an applied stress and recovers at least a part of said strain in an isothermal phase transformation when said applied stress is removed.

5. The catheter as recited in claim 1 wherein said distal tube is attached to said proximal shaft by an insert and an extension tube, said extension tube having an inner wall and an outer wall, with said outer wall affixed to said distal tube, and said insert affixed to said inner wall of said extension tube and said proximal shaft, and wherein said extension is attached to said proximal shaft by said insert and said extension tube, said extension affixed to said outer wall of said extension tube.

6. The catheter as recited in claim 5 wherein said extension has a ribbon shape.

7. The catheter as recited in claim 5 wherein said insert and said extension tube are made from a superelastic material which undergoes an isothermal phase transformation at said ambient body vessel temperature, T when strained in response to an applied stress and recovers at least a part of said strain in an isothermal phase transformation when said applied stress is removed.

8. The catheter as recited in claim 7 wherein said proximal shaft is made from stainless steel.

9. The catheter as recited in claim 1 wherein said shaft is a cylindrical tube having an outer surface, and wherein a portion of said outer surface at the distal end of said shaft is formed as a concave surface.

10. The catheter as recited in claim 1 wherein said extension is a core wire.

11. The catheter as recited in claim 1 wherein said proximal shaft is made of a superelastic material which undergoes an isothermal phase transformation at said ambient body vessel temperature, T when strained in response to an applied stress and recovers at least a part of said strain in an isothermal phase transformation when said applied stress is removed to provide shape retention to said catheter.

12. The catheter as recited in claim 1 wherein said superelastic material is a nickel-titanium alloy.

13. The catheter as recited in claim 1 wherein the superelastic material is a copper-base alloy.

14. The catheter as recited in claim 1 further comprising a balloon attached to said distal tube.

15. The catheter as recited in claim 1 wherein said proximal shaft is tubular shaped.

16. The catheter as recited in claim 1 wherein said distal tube is made of a polymer material, said polymer material selected from the group consisting of PEBA, PET, Polyurethane, Polyethylene and nylon.

17. The catheter as recited in claim 1 wherein said superelastic material has an isothermal austenite to martensite phase transformation at said ambient temperature, T when strained in response to an applied stress.

18. The catheter as recited in claim 1 wherein said superelastic material has an austenite to martensite phase transformation temperature, $T_M$, below said ambient body vessel temperature, $T_M<T$.

* * * * *

UNITED STATES PATENT AND TRADEMARK OFFICE
CERTIFICATE OF CORRECTION

PATENT NO. : 6,685,720 B1
DATED : February 3, 2004
INVENTOR(S) : Show-Mean Wu and Richardo Roman It is certified that error appears in the above-identified patent and that said Letters Patent is hereby corrected as shown below:

<u>Title page, Item [54] and Column 1, line 1,</u>
Delete "SHAPED" insert -- SHAPE --

<u>Column 8,</u>
Line 19, in between the words "ambient" and "temperature" insert -- body vessel --

Signed and Sealed this

Thirteenth Day of April, 2004

JON W. DUDAS
*Acting Director of the United States Patent and Trademark Office*